United States Patent
Lin et al.

(10) Patent No.: US 8,058,362 B2
(45) Date of Patent: Nov. 15, 2011

(54) MANUFACTURE OF NOVEL EPOXY RESINS SEMI-THERMOSETS AND THEIR HIGH TG THERMOSETS FOR ELECTRONIC APPLICATIONS

(75) Inventors: Ching-Hsuan Lin, Taichung (TW); Yu Ming Hu, Taichung (TW); Hong Tze Lin, Taichung (TW)

(73) Assignee: National Chung Hsing University, Taichung (TW)

( * ) Notice: Subject to any disclaimer, the term of this patent is extended or adjusted under 35 U.S.C. 154(b) by 378 days.

(21) Appl. No.: 12/388,996

(22) Filed: Feb. 19, 2009

(65) Prior Publication Data
US 2009/0215967 A1  Aug. 27, 2009

(30) Foreign Application Priority Data
Feb. 21, 2008  (TW) .............................. 97106137 A

(51) Int. Cl.
C07D 498/00 (2006.01)
C08G 59/14 (2006.01)
C08L 63/00 (2006.01)
C08L 63/02 (2006.01)
C08L 63/04 (2006.01)

(52) U.S. Cl. ........ 525/505; 525/481; 525/504; 525/508; 525/523; 525/533; 528/108; 544/90

(58) Field of Classification Search .................. None
See application file for complete search history.

(56) References Cited

U.S. PATENT DOCUMENTS
6,291,627 B1    9/2001  Wang et al.
7,053,138 B2 *  5/2006  Magendie et al. ............. 523/451
7,566,780 B2 *  7/2009  Lin et al. ......................... 544/90

OTHER PUBLICATIONS

Sponton et al., "Development of a DOPO-containing benzoxazine and its high-performance flame retardant copolybenzoxazines," Polymer Degradation and Stability, vol. 94, Jul. 1, 2009, pp. 1693-1699.*

* cited by examiner

Primary Examiner — Robert Sellers
(74) Attorney, Agent, or Firm — Rothwell, Flgg, Ernst & Manbeck, P.C.

(57) ABSTRACT

An active-hydrogen-containing (carboxyl or hydroxyl) phosphorus compound is provided. An epoxy resin semi-thermoset formed by bonding the phosphorus compound to an epoxy group is also provided. A flame-retardant epoxy resin thermoset is formed after reacting the epoxy resin semi-thermoset with a curing agent. The epoxy resin thermoset possesses excellent flame retardancy, heat stability, and high glass transition temperature (Tg), does not produce toxic and corrosive fumes during combustion, and thus is an environmentally friendly flame-retardant material.

24 Claims, 4 Drawing Sheets

MANUFACTURE OF NOVEL EPOXY RESINS SEMI-THERMOSETS AND THEIR HIGH TG THERMOSETS FOR ELECTRONIC APPLICATIONS

CROSS REFERENCE TO RELATED APPLICATION(S)

This application claims the benefit of Taiwan Application No. TW 097106137, filed Feb. 21, 2008, of which is incorporated by reference in its entirety

FIELD OF THE INVENTION

The present invention relates to an active-hydrogen-containing phosphorus compound. The present invention also relates to an epoxy resin semi-thermoset formed by bonding the phosphorus compound to an epoxy group, and a cured epoxy resin thermoset thereof. The epoxy resin thermoset possesses excellent flame retardancy, heat stability, and high glass transition temperature (Tg).

DESCRIPTION OF THE PRIOR ART

In recent years, polymer materials have become more and more widely used, and in such polymer materials epoxy resin thermosets are widely used in printed circuit boards (PCB) and electronic packaging materials (EPM) due to their excellent solvent resistance, superior electrical isolation, and good dimension stability. However, as the component elements of an epoxy resin include carbon, hydrogen, and oxygen, epoxy resins are easily combustible, which is their main disadvantage in application. With the containing development of the electronic industry, the gradual advances in technology require that products be more and more light, thin, short, and small. However, the conventional pin through hole (PTH) has been developed and become part of a surface mount technology (SMT), for example, package methods, such as ball grid arrays (BGA), flip chip packages, and chip size packages (CSP), which have rapidly driven the progress in printed circuit board technology towards "high density" and "multi-layer". Moreover, the requirements of the semi-conductor industry in terms of high temperature resistance and flame retardancy of materials are becoming stricter, for example, the electronic materials are required to reach a UL-94 grade of V-0, so the need for improved flame retardancy of epoxy resin thermosets is also an inevitable tendency.

Halogen and antimony oxide based epoxy resin flame retardants are widely used in the epoxy resins of earlier flame-retardant printed circuit boards, in which tetrabromobisphenol is a main halogen flame-retardant additive. However, the epoxy resin thermosets containing halogen flame retardants have an obvious disadvantage, that is, when they are combusted at inappropriate temperature, hazardous carcinogenic gases such as dioxin and benzofuran are generated, in addition to the corrosive gas generated during combustion. Therefore, the development of a novel flame retardant that replaces halogen with other elements is a major goal of current research.

In recent years, the searches suggest that for polymers, organic phosphorus compounds have preferable flame-retardant properties, and compared with halogen-containing flame retardant, an organic phosphorus compound in a solid state can retard flame, and will not generate fumes or poisonous gases. In addition to reducing the mechanical properties of the epoxy resin thermoset, the conventional additive flam retardant suffers from a decrease in flame-retardant effects due to the mobility or volatilization of flame retardant molecules. Therefore, the polymer will have a more preferable flame-retardant effect, when a reactive organic phosphorus group is introduced into the polymer structure.

U.S. Pat. No. 6,291,627 B1 discloses that a phosphorus-containing epoxy resin semi-thermoset is synthesized by reacting the active hydrogen of 9,10-dihydro-9-oxa-10-phosphaphenanthrene-10-oxide (DOPO) with an epoxy resin, and that a phosphorus-containing epoxy resin thermoset is formed by reacting the semi-thermoset with curing agents such as diaminodiphenyl sulfone (DDS), dicyandiamide (DICY) and phenol novolac (PN). Furthermore, the results show that this phosphorus-containing epoxy resin thermoset has high heat stability and flame retardancy. However, the reaction of DOPO with the epoxy group of an epoxy resin will decrease the functionality of the epoxy resin, thus leading to the fact that the crosslink density of the epoxy resin thermoset decreases with the increase of the amount of DOPO introduced, and the glass transitional temperature (Tg) also decreases with the decrease of the crosslink density of the epoxy resin thermoset.

The present invention provides a phosphorus-containing benzoxazine monomer with a carboxyl or hydroxyl containing an active hydrogen, where the monomer can be bonded to the epoxy group of an epoxy resin through the position of the active hydrogen, to synthesize a phosphorus-containing epoxy resin semi-thermoset containing benzoxazine. The functional group of benzoxazine in the epoxy resin semi-thermoset can perform a ring-opening reaction by heating, self ring-opening reaction, or being bonded to an epoxy resin to provide additional crosslink points, so as to improve the thermal resistant property of the epoxy resin thermoset, and exhibit a flame-retardant property reaching a UL-94 grade of V-0. In view of the disadvantages in prior art, the present invention results in a phosphorus-containing epoxy resin semi-thermoset capable of increasing the crosslink density without any loss of total crosslink points for reaction. In such manner, the impact on the thermal resistant property caused by the introduction of the phosphorus element can be effectively alleviated.

SUMMARY OF THE INVENTION

The present invention provides a novel phosphorous-containing compound of formula I:

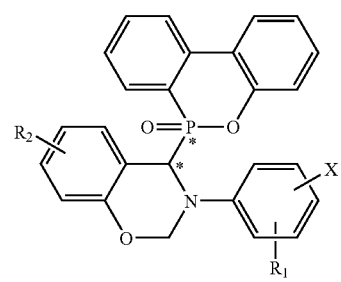

where:

$R_1$ and $R_2$ are independently H, $C_1$-$C_4$ alkyl, $CF_3$, $OCF_3$, phenyl, halogen, phenoxy, $C_3$-$C_7$ cycloalkyl, or $C_1$-$C_4$ alkoxy; and X is carboxyl or hydroxyl.

The present invention further provides a process for preparing the compound of formula I, including:
(i) reacting

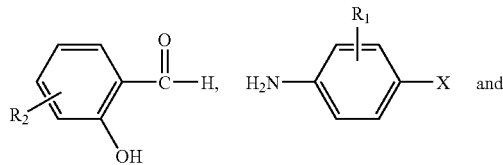 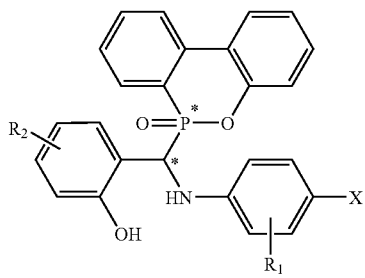

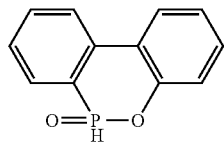

to generate a compound of formula II:

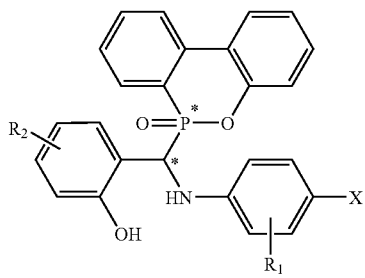

II where $R_1$, $R_2$ and X are defined as above; and
(ii) reacting the compound of formula II with formaldehyde or paraformaldehyde to generate the compound of formula I.

The present invention further provides phosphorous flame-retardant epoxy resin semi-thermosets of formulae (a) to (f):

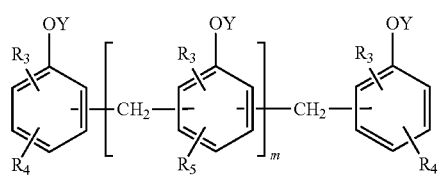 (a)

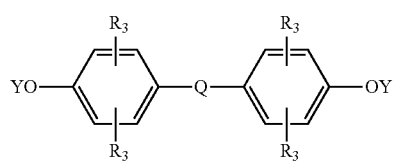 (b)

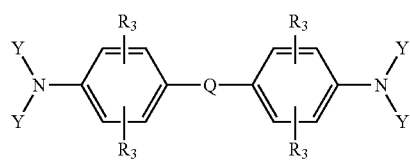 (c)

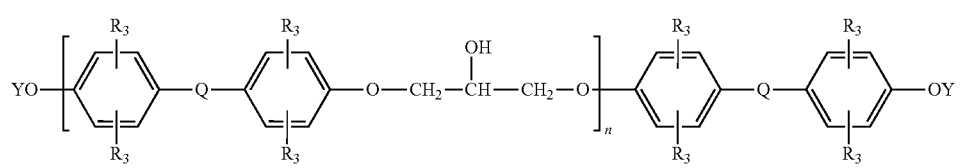 (d)

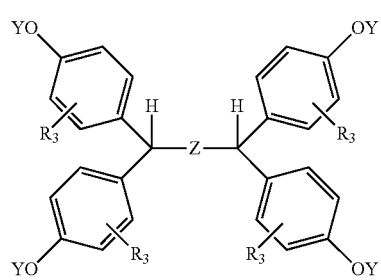 (e)

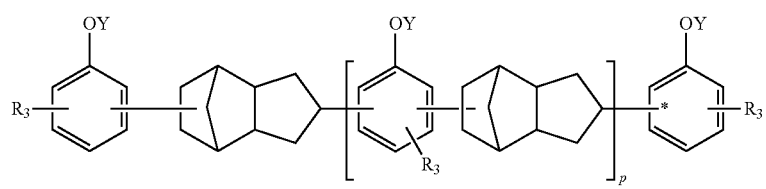 (f)

where:
m is an integer or decimal with a value ranging from 1 to 12;
n is an integer or decimal with a value ranging from 0 to 15;
p is an integer or decimal with a value ranging from 0 to 5;
$R_3$ is H, $C_1$-$C_4$ alkyl or $C_1$-$C_4$ alkoxy;
$R_4$ and $R_5$ are independently H, $C_1$-$C_4$ alkyl, $C_1$-$C_4$ alkoxy or

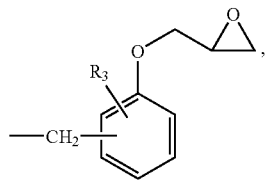

where $R_3$ is defined as above;
Q is

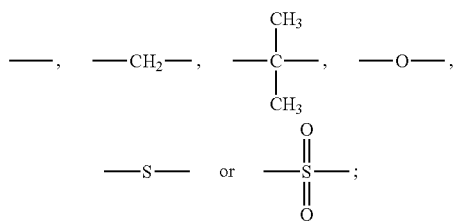

Z is

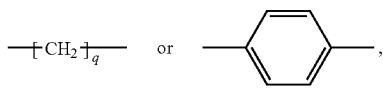

where q is an integer or decimal with a value ranging from 0 to 6; and

Y is A or B, and at least one of Y is B, where:
A is

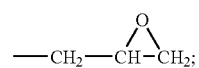

and
B is

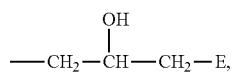

where
E is

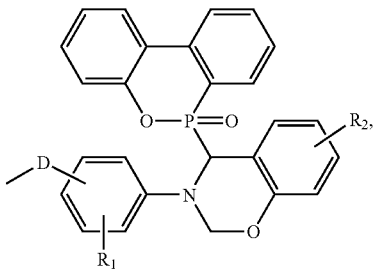

where:
$R_1$ and $R_2$ are defined as above; and
D is an ether group (—O—) or an ester group (—COO—).

In a preferred embodiment of the present invention, the flame-retardant epoxy resin semi-thermoset has a structural formula of (a), and $R_3$ is methyl and $R_4$ is H.

In another preferred embodiment of the present invention, the flame-retardant epoxy resin semi-thermoset has a structural formula of (b), and Q is —C(CH$_3$)$_2$—.

The present invention further provides a process for preparing the phosphorous flame-retardant epoxy resin semi-thermosets of formulae (a) to (f), including reacting the compound of formula I with the epoxy resins of formulae (a') to (f'):

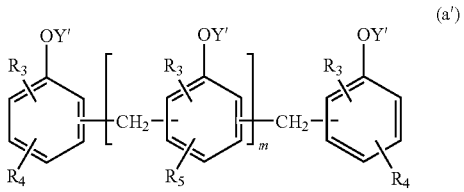
(a')

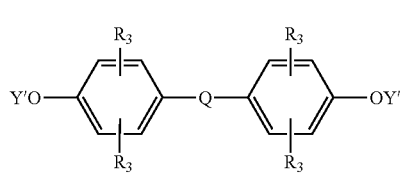
(b')

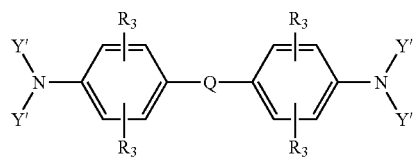
(c')

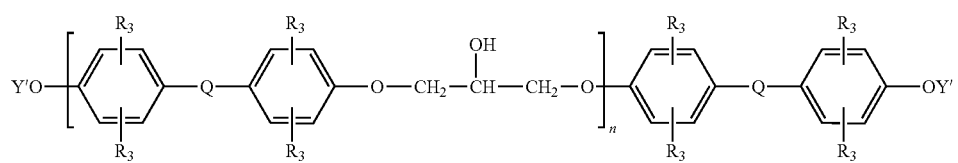
(d')

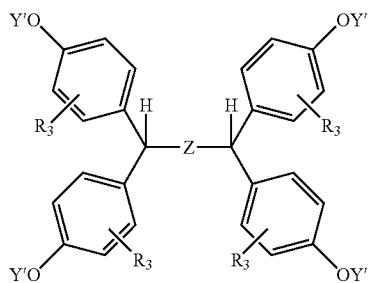

where m, n, p, $R_3$, $R_4$, $R_5$, Q and Z are defined as above; and Y' is

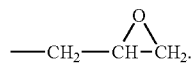

The present invention further provides a phosphorous flame-retardant epoxy resin thermoset which is produced by curing the phosphorous flame-retardant epoxy resin semi-thermoset of the present invention.

DETAILED DESCRIPTION

Figure 1:
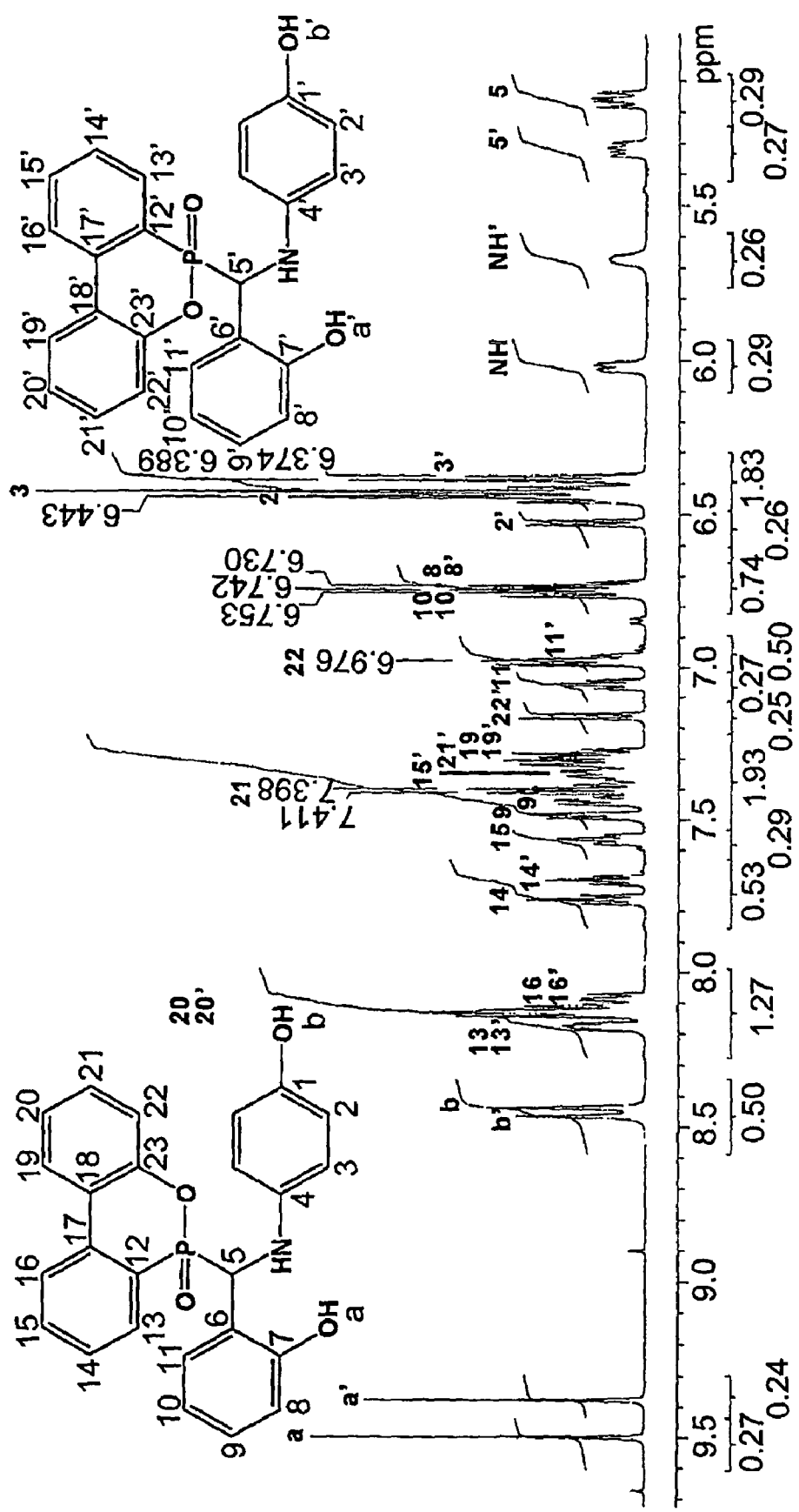
FIG. 1 is a $^1$H NMR spectrum of compound (2).

In order to make the features and advantages of the present invention more apparent and easily understood, preferred embodiments are exemplified in detail with reference to the accompanying drawings:

In the present invention, 2-hydroxybenzaldehyde is first reacted with mono functional amine, 4-aminophenol or 4-aminobenzoic acid (compound (1) or (4)), to form a compound containing Schiff base linkage. Next, a C=N double bond of the compound is reduced by DOPO, thus resulting in a diastereoisomer having P and C chiral centers (compound (2) or (5)), i.e., a compound having a phenol group and a secondary amine). And then, compound (2) or (5) is further reacted with formaldehyde to generate benzoxazine (compound (3) or (6)):

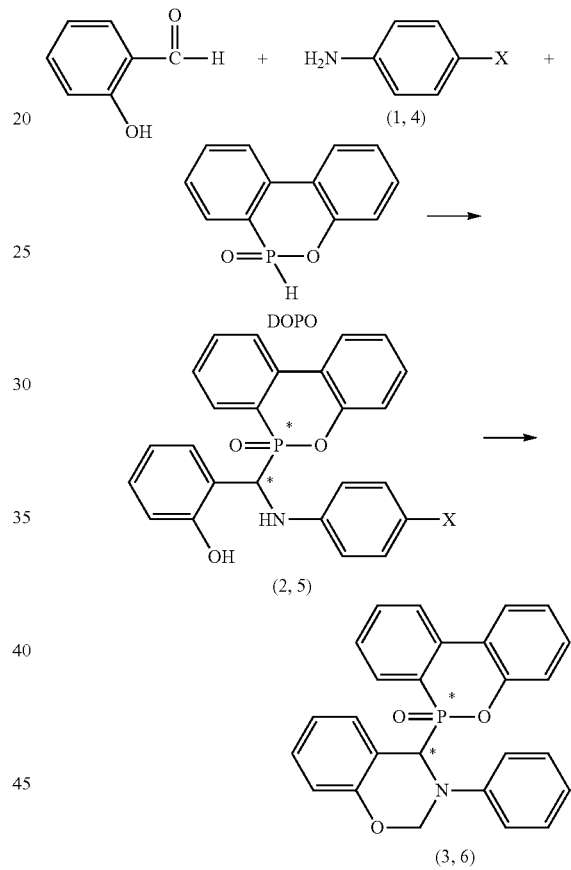

where X in compounds (1), (2) and (3) is hydroxyl, and X in compounds (4), (5) and (6) is carboxyl.

Then, compounds (3) and (6), used as epoxy resin modifiers, are separately reacted with cresol novolac epoxy (CNE), to generate epoxy resin semi-thermosets (7) and (8), and the reaction is as follows:

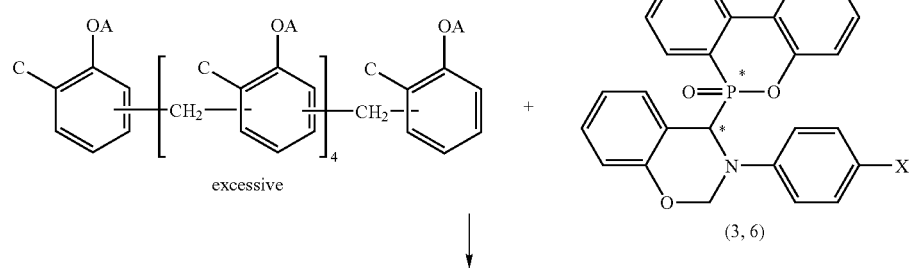

-continued

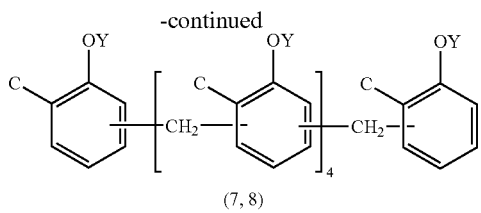

(7, 8)

Y in compounds (7) and (8) is A or B, and at least one of Y is B;

A is

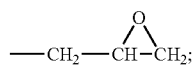

B is

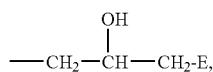

in which E is

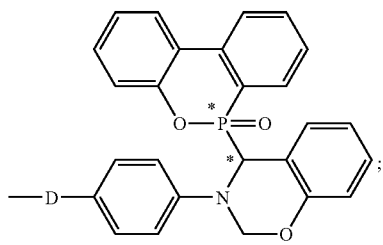

where D in compound (7) is an ether group (—O—) and D in compound (8) is an ester group (—COO—).

It is necessary to adjust the proportion of the synthesized compounds (3) and (6) to the epoxy resin when they are reacted, so as to limit the phosphorus content in the product to a range of 0.5 wt % to 4 wt %, and preferably to a range of 1 wt % to 2 wt %.

The reaction between compound (3) or (6) and CNE can be carried out at a temperature in the range of 100° C. to 200° C., and preferably in the range of 120° C. to 170° C. The reaction can also be carried out with or without a small amount of a catalyst, and the useful catalysts include phenylimidazole, 2-methyl imidazole, triphenylphosphine, or suitable quarternary phosphonium compounds, or quarternary ammonium compounds. The quarternary phosphonium compounds include, but are not limited to, ethyltriphonelphosphonium iodide, ethyltriphonelphosphonium chloride, ethyltriphonelphosphonium bromide, and so on. The quarternary ammonium compounds include, but are not limited to, benzyltrimethylammonium chloride, benzyltriethylammonium chloride, tetrabutylammonium chloride, and so on. The formed flame-retardant epoxy resin semi-thermoset is useful in the fabrication of circuit boards.

Epoxy resin semi-thermosets ((7) and (8)) can be automatically cured or cured by heating after being mixed with a curing agent. The curing agents useful in the present invention include, but are not limited to, phenol novolac, dicyandiamide, diaminodiphenyl methane, diaminodiphenyl sulfone, phthalic anhydride, hexahydrophthalic anhydride, and so on. The curing temperature useful in the present invention is higher than 150° C. The formed flame-retardant epoxy thermoset is useful in the fabrication of printed circuit boards or semi-conductor package materials. Epoxy resins suitable for the production of the flame-retardant epoxy semi-thermoset and thermoset of the present invention include any epoxy resin, such as bi-functional epoxides of bisphenol A, bisphenol F, bisphenol S, biphenol, or a mixture thereof, and also include phenol formaldehyde novolac, cresol formaldehyde novolac, or a mixture thereof.

The following preferred embodiments are provided for the purpose of illustrating the principles of the present invention only, but do not limit the scope of the present invention; for example, phosphorus-containing flame-retardant epoxy semi-thermosets having different structures can also be prepared with other epoxy resins through similar reactions. Therefore, compounds obtained according to the following embodiments with slight modification or extensions fall within the scope of the present invention.

EMBODIMENTS

The implementation of the invention described above is illustrated with reference to the following embodiments.

I. Preparation of Phosphorous-containing Benzoxazine

Example 1

Preparation of Precursor (2) of Phosphorous-containing Benzoxazine 60 mmol (6.55 g) of 4-aminophenol, 60 mmol (7.33 g) of 2-hydroxylbenzaldehyde, and 60 mmol (12.97 g) of DOPO were added to a 250 ml single-neck round-bottom reactor containing 150 ml of dimethyl formamide (DMF). After reacting at room temperature for 12 hours, a white powder was separated out. After the completion of the reaction, the reaction solution was poured directly into 1000 ml deionized water, separated and washed to remove the DMF, and filtered by a suction filter. The resultant filter cake was dried at 110° C. with a vacuum oven to obtain 24.52 g of a product in the form of a tan powder. The yield is 95%, and the melting point of the product is 147° C. A $^1$H NMR spectrum of compound (2) is shown in FIG. 1.

Example 2

Figures 2A, 2B:
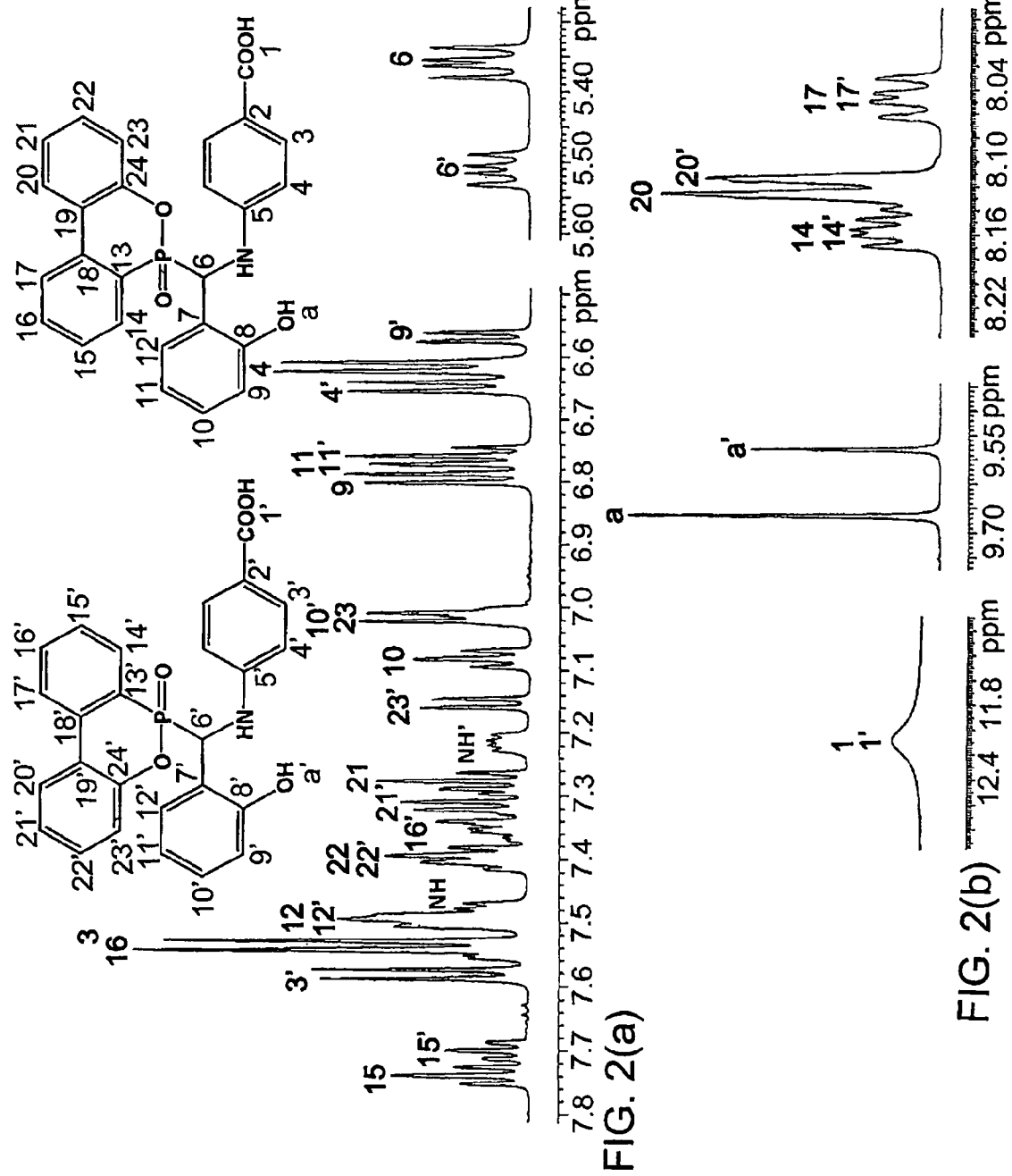
FIG. 2 is $^1$H NMR spectra (a) 5.3-7.8 ppm (b) 8-12.8 ppm of compound (5).

Preparation of Precursor (5) of Phosphorous-containing Benzoxazine 0.1 mol (13.71 g) of 4-aminobenzoic acid, 0.1 mol (12.21 g) of 2-hydroxylbenzaldehyde, and 0.1 mol (21.62 g) of DOPO were added to a 500 ml single-neck round-bottom reactor containing 200 ml of DMF. After reacting at room temperature for 12 hours, a pale yellow powder was separated out. After the completion of the reaction, the reaction solution was poured directly into 1000 ml deionized water, separated and washed to remove the DMF, and filtered by a suction filter. The resultant filter cake was dried at 110° C. with a vacuum oven to obtain 44.9 g of a product in the form of a white powder. The yield is 98%, and the melting point of the product is 200° C. A $^1$H NMR spectrum of compound (5) is shown in FIG. 2.

Example 3

Preparation of Phosphorous-containing Benzoxazine (3)

Figure 3:
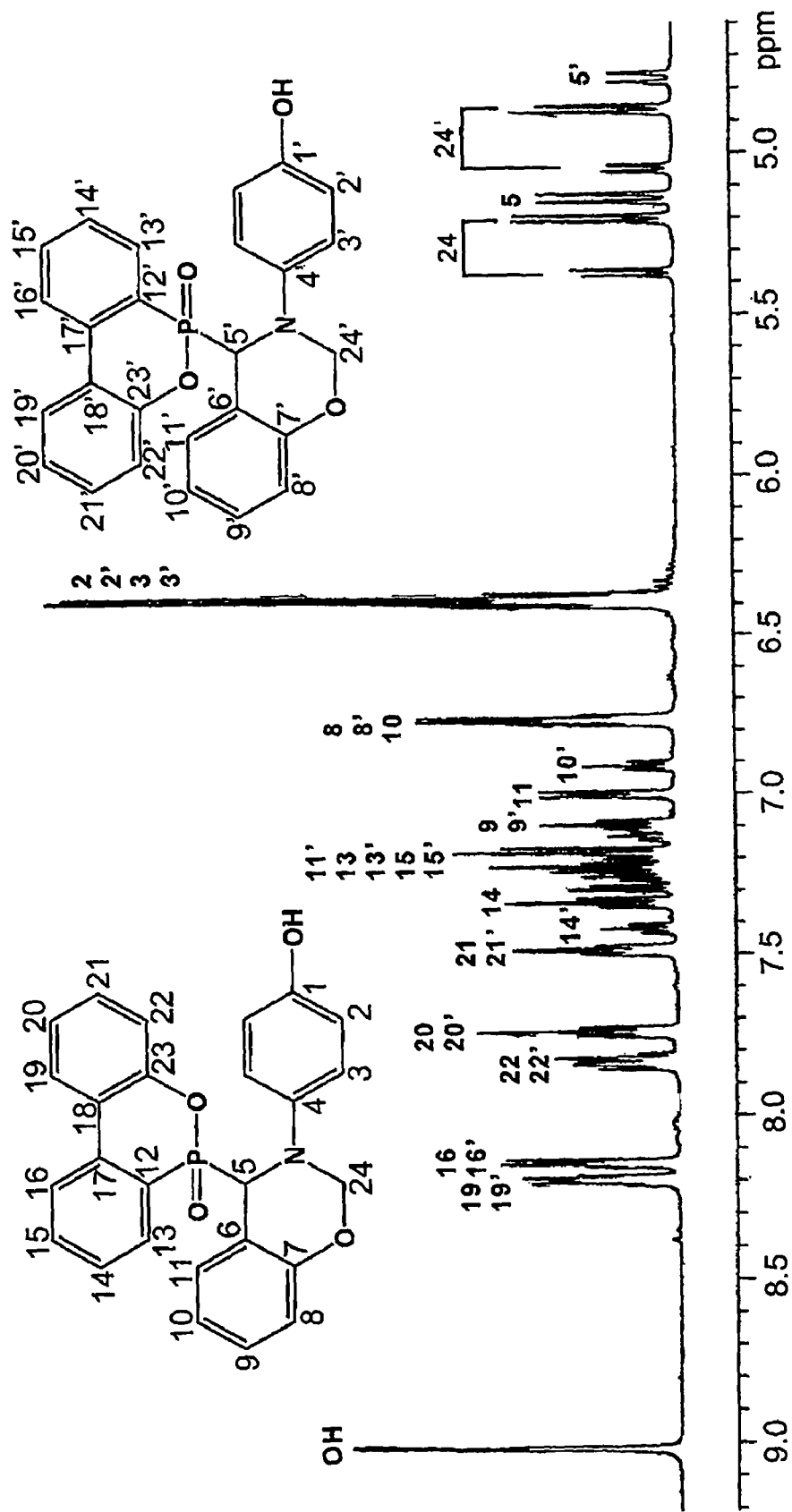
FIG. 3 is a $^1$H NMR spectrum of compound (3).

0.1 mol (42.94 g) of compound (2) was added to a 500 ml single-neck round-bottom reactor containing 300 ml of acetone. 0.11 mol (8.9 g) of formaldehyde (37% aqueous solution) was dropped into the reactor. After reacting at room temperature for 4 hours, the temperature was raised to reflux temperature, and the reaction was continued for 12 hours. After the completion of the reaction, the reaction solution was poured directly into 1000 ml deionized water, separated and washed, and filtered by a suction filter. The resultant filter cake was dried at 110° C. with a vacuum oven, to obtain 41.7 g of a product. The yield is 94%, the melting point of the product is 222° C. and 238° C., and the exothermic peak is from 240° C. to 270° C. A $^1$H NMR spectrum of compound (3) is shown in FIG. 3.

Example 4

Preparation of Phosphorous-containing Benzoxazine (6)

Figures 4A, 4B:
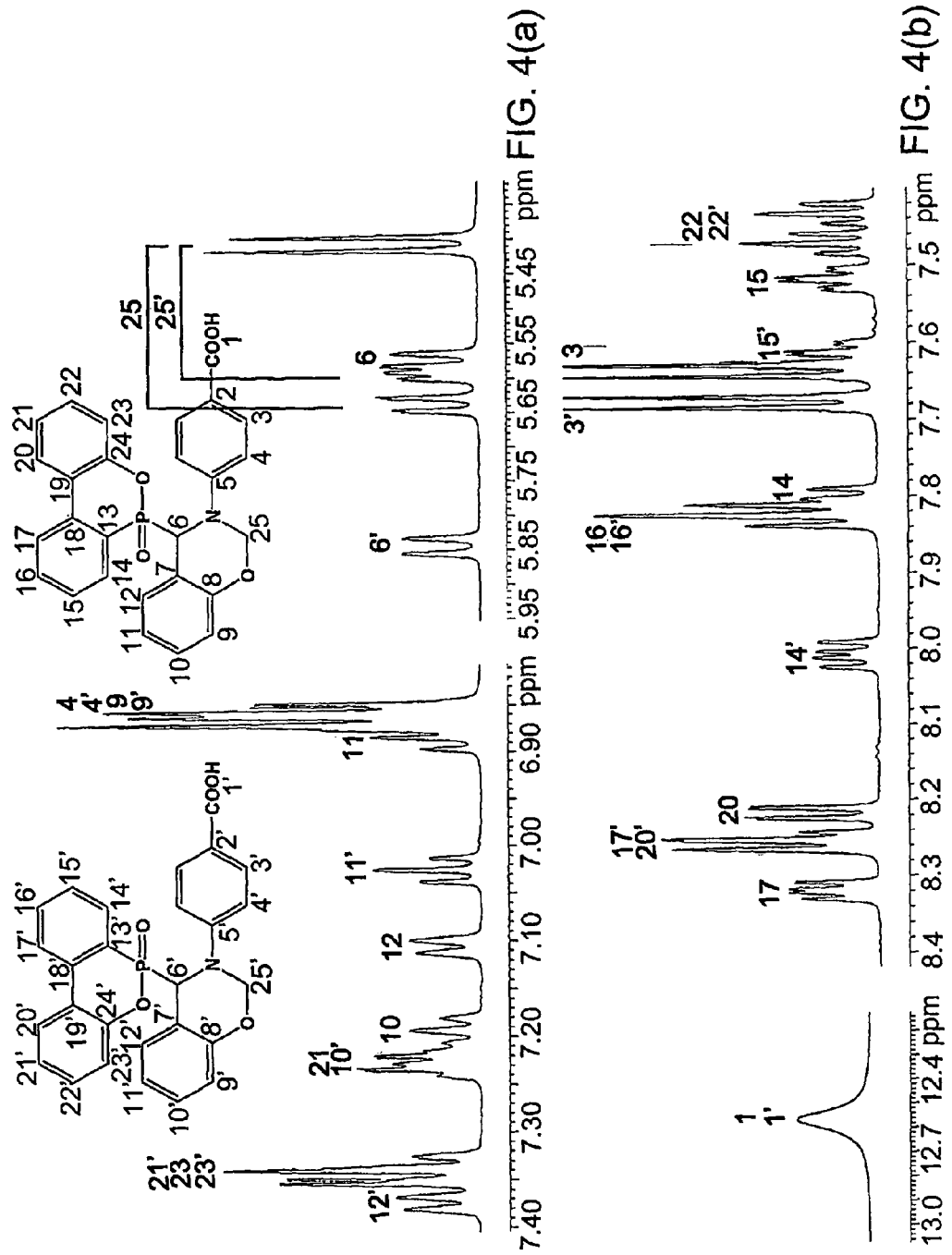
FIG. 4 is $^1$H NMR spectra (a) 5.4-7.4 ppm (b) 7.4-13.0 ppm of compound (6).

0.1 mol (45.74 g) of compound (5) was added into a 500 ml single-neck round-bottom reactor containing 300 ml of acetone. 0.11 mol (8.9 g) of formaldehyde (37% aqueous solution) was dropped into the reactor. After reacting at room temperature for 5 hours, the temperature was raised to reflux temperature, and the reaction was continued for 12 hours. After the completion of the reaction, the reaction solution was poured directly into 1000 ml deionized water, separated and washed, and filtered by a suction filter. The resultant filter cake was dried at 110° C. with a vacuum oven to obtain 43.48 g of a product. The yield is 92%, the melting point of the product is 248° C., and the exothermic peak is from 255° C. to 280° C. A $^1$H NMR spectrum of compound (6) was shown in FIG. 4.

II. Preparation of Phosphorus Group-containing Epoxy Resin Semi-Thermoset

Example 5

Preparation of Semi-thermoset (7-1.0) with a Phosphorus Content of 1%

10 g of CNE (epoxide equivalent weight, EEW=200 g/eq) was added to a 100 ml three-neck round-bottom reactor with the introduction of nitrogen and a condenser tube connected to the mouthpieces thereof. The reaction mixture was stirred by a hot plate/stirrer and heated to 160° C. by an oil bath. 1.66 g of phosphorus-containing benzoxazine (3) was added to the reactor and reacted for 2.5 hours to get a transparent sticky liquid. An epoxy resin semi-thermoset with EEW 268 g/eq was obtained after cooling (252 g/eq theoretically).

Example 6

Preparation of Semi-thermoset (7-1.5) with a Phosphorus Content of 1.5%

The reaction conditions were the same as those in Example 5, except that 2.71 g rather than 1.66 g of phosphorus-containing benzoxazine (3) was used. An epoxy resin semi-thermoset with EEW 309 g/eq was obtained after cooling (290 g/eq theoretically).

Example 7

Preparation of Semi-thermoset (7-2.0) with a Phosphorus Content of 2%

The reaction conditions were the same as those in Example 5, except that 3.98 g rather than 1.66 g of phosphorus-containing benzoxazine (3) was used. An epoxy resin semi-thermoset with EEW 366 g/eq was obtained after cooling (341 g/eq theoretically).

Example 8

Preparation of Semi-thermoset (7-2.5) with a Phosphorus Content of 2.5%

The reaction conditions were the same as those in Example 5, except that 5.52 g rather than 1.66 g of phosphorus-containing benzoxazine (3) was used. An epoxy resin semi-thermoset with EEW 443 g/eq was obtained after cooling (414 g/eq theoretically).

Example 9

Preparation of Semi-thermoset (8-1.0) with a Phosphorus Content of 1%

10 g of CNE (epoxide equivalent weight, EEW=200 g/eq) was added to a 100 ml three-neck round-bottom reactor with the introduction of nitrogen and a condenser tube connected to the mouthpieces thereof. The reaction mixture was stirred by a hot plate/stirrer and heated to 150° C. by an oil bath. 1.78 g of phosphorus-containing benzoxazine (6) was added to the reactor and reacted for 80 minutes to get a transparent sticky liquid. An epoxy resin semi-thermoset with EEW 277 g/eq was obtained after cooling (255 g/eq theoretically).

Example 10

Preparation of Semi-thermoset (8-1.5) with a Phosphorus Content of 1.5%

The reaction conditions were the same as those in Example 9, except that 2.94 g rather than 1.78 g of phosphorus-containing benzoxazine (6) was used. An epoxy resin semi-thermoset with EEW 322 g/eq was obtained after cooling (value is 295 g/eq theoretically).

Example 11

Preparation of Semi-thermoset (8-2.0) with a Phosphorus Content of 2%

The reaction conditions were the same as those in Example 9, except that 4.34 g rather than 1.78 g of phosphorus-containing benzoxazine (6) was used. An epoxy resin semi-thermoset with EEW 382 g/eq was obtained after cooling (252 g/eq theoretically).

Example 12

Preparation of Semi-thermoset (8-2.5) with a Phosphorus Content of 2.5%

The reaction conditions were the same as those in Example 9, except that 6.01 g rather than 1.78 g of phosphorus-containing benzoxazine (6) was used. An epoxy resin semi-thermoset with EEW 465 g/eq was obtained after cooling (434 g/eq theoretically).

Example 13

Preparation of Semi-thermoset (9-1.0) with a Phosphorus Content of 1%

10 g of diglycidyl ether of bisphenol A (DGEBA, epoxide equivalent weight, EEW=188 g/eq) was added to a 100 ml three-neck round-bottom reactor with the introduction of nitrogen and a condenser tube connected to the mouthpieces thereof. The reaction mixture was stirred by a hot plate/stirrer and heated to 150° C. by an oil bath. 1.66 g of phosphorus-containing benzoxazine (3) was added to the reactor and reacted for 2.5 hours to get a transparent sticky liquid. An epoxy resin in a solid state with EEW 232 g/eq was obtained after cooling (235 g/eq theoretically).

Example 14

Preparation of Semi-thermoset (9-1.5) with a Phosphorus Content of 1.5%

The reaction conditions were the same as those in Example 13, except that 2.71 g rather than 1.66 g of phosphorus-containing benzoxazine (3) was used. An epoxy resin semi-thermoset with EEW 298 g/eq was obtained after cooling (270 g/eq theoretically).

Example 15

Preparation of Semi-thermoset (9-2.0) with a Phosphorus Content of 2%

The reaction conditions were the same as those in Example 13, except that 3.98 g rather than 1.66 g of phosphorus-containing benzoxazine (3) was used. An epoxy resin semi-thermoset with EEW 349 g/eq was obtained after cooling (316 g/eq theoretically).

Example 16

Preparation of Semi-thermoset (9-2.5) with a Phosphorus Content of 2.5%

The reaction conditions were the same as those in Example 13, except that 5.52 g rather than 1.66 g of phosphorus-containing benzoxazine (3) was used. An epoxy resin semi-thermoset with EEW 408 g/eq was obtained after cooling (381 g/eq theoretically).

III Epoxy Resin Thermoset

Example 17

Preparation of Epoxy Resin Thermoset

Equal equivalent of 4,4-diaminodiphenyl sulfone (DDS) or phenol novolac (PN) used as a curing agent were added to the epoxy resin semi-thermosets synthesized in Examples 5 to 16. The mixture was first ground into powder, then heated to 150° C. so that it goes into a melting state, stirred to be uniform and then put into an oven to cure. The curing operation was conducted at 180° C. for 2 hours, at 200° C. for 2 hours, or at 220° C. for 2 hours. Table 1 shows the results for glass transition temperature (Tg) and UL-94 flame-retardant tests of the epoxy resin thermoset prepared in Example 17.

TABLE 1

| Samples Epoxy resin/curing agent | Phosphorus content % | Nitrogen content % | Glass transition temperature (Tg, ° C.) | UL-94 grade |
|---|---|---|---|---|
| CNE/DDS | 0 | 2.09 | 256 | V-2 |
| (7-1.0)/DDS | 0.82 | 2.52 | 237 | V-0 |
| (7-1.5)/DDS | 1.26 | 2.48 | 220 | V-0 |
| (7-2.0)/DDS | 1.73 | 2.43 | 198 | V-0 |
| (8-1.0)/DDS | 0.83 | 2.46 | 225 | V-0 |
| (8-1.5)/DDS | 1.27 | 2.42 | 209 | V-0 |
| (8-2.0)/DDS | 1.74 | 2.37 | 202 | V-0 |
| DGEBA/DDS | 0 | 2.09 | 190 | V-2 |
| (9-1.0)/DDS | 0.82 | 2.36 | 185 | V-0 |
| (9-1.5)/DDS | 1.44 | 2.27 | 165 | V-0 |
| (9-2.0)/DDS | 1.76 | 2.14 | 162 | V-0 |
| (9-2.5)/DDS | 2.29 | 1.96 | 160 | V-0 |
| CNE/PN | 0 | 0 | 217 | V-2 |
| (7-1.0)/PN | 0.72 | 0.32 | 200 | V-1 |
| (7-1.5)/PN | 1.12 | 0.51 | 192 | V-0 |
| (7-2.0)/PN | 1.55 | 0.70 | 181 | V-0 |
| (8-1.0)/PN | 0.73 | 0.33 | 197 | V-1 |
| (8-1.5)/PN | 1.13 | 0.51 | 191 | V-0 |
| (8-2.0)/PN | 1.57 | 0.71 | 182 | V-0 |
| DGEBA/PN | 0 | 0 | 151 | V-2 |
| (9-1.0)/PN | 0.73 | 0.33 | 157 | V-2 |
| (9-1.5)/PN | 0.77 | 0.53 | 152 | V-1 |
| (9-2.0)/PN | 0.81 | 0.73 | 150 | V-1 |
| (9-2.5)/PN | 0.89 | 0.98 | 148 | V-0 |

It can be seen from the results in Table 1 that the phosphorus-containing epoxy resin thermoset of the present invention has a high Tg, when the flame-retardant effect reaches a UL-94 grade of V-0. For example, when a UL-94 grade of V-0 is reached, the Tg of the (7)/DDS cured system is as high as 237° C., the Tg of the (8)/DDS cured system is as high as 225° C., and the Tg of the (9)/DDS cured system is as high as 185° C. Therefore, the phosphorus-containing epoxy resin thermoset of the present invention is very suitable for the production of high-Tg circuit board substrates, semi-conductor package materials, and other relevant works.

The claims below are intended to define the rational protection scope of the present invention. However, it should be understood that obvious modifications made by persons having ordinary skill in the art according to the disclosure of the present invention also fall within the reasonable protection scope of the present invention.

What is claimed is:

1. A compound of formula I:

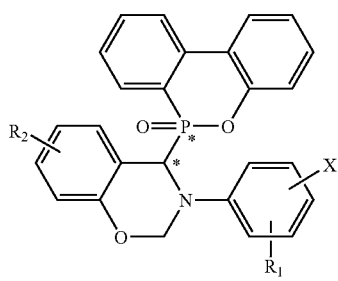

I wherein:
$R_1$ and $R_2$ are independently H, $C_1$-$C_4$ alkyl, $CF_3$, $OCF_3$, phenyl, halogen, phenoxy, $C_3$-$C_7$ cycloalkyl, or $C_1$-$C_4$ alkoxy; and
X is carboxyl or hydroxyl.

2. The compound of formula I according to claim 1, being an epoxy resin modifier.

3. A process for preparing a compound of formula I according to claim 1, comprising:
(i) reacting

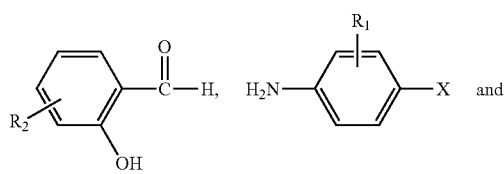

and

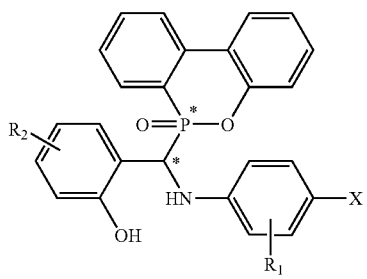

to generate a compound of formula II:

II wherein $R_1$, $R_2$ and X are as defined in claim 1; and
(ii) reacting the compound of formula II with formaldehyde or paraformaldehyde to generate the compound of formula I.

4. A phosphorus-containing flame-retardant epoxy resin semi-thermoset, having a structure selected from the group consisting of formulae (a) to (f):

(a)

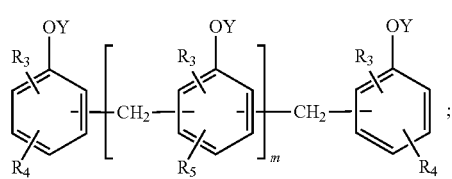

(b)

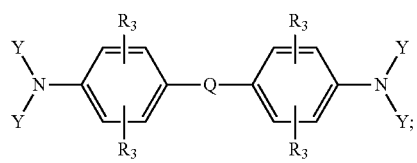

(c)

(d)

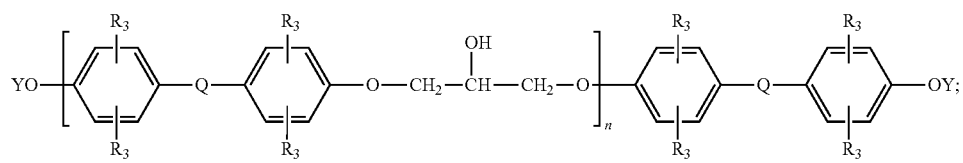

(e)

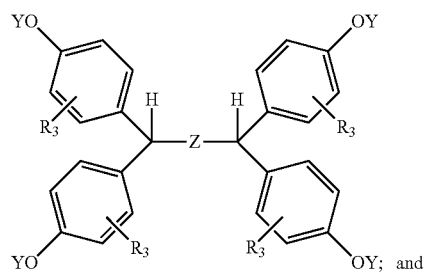

-continued

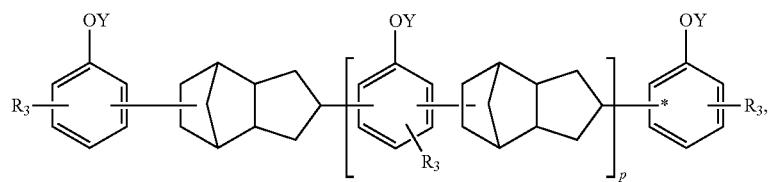
(f)

wherein:
  m is an integer or decimal with a value ranging from 1 to 12;
  n is an integer or decimal with a value ranging from 0 to 15;
  p is an integer or decimal with a value ranging from 0 to 5;
  $R_3$ is H, $C_1$-$C_4$ alkyl or $C_1$-$C_4$ alkoxy;
  $R_4$ and $R_5$ are independently H, $C_1$-$C_4$ alkyl, $C_1$-$C_4$ alkoxy or

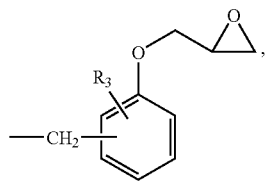

wherein $R_3$ is defined as above;
Q is

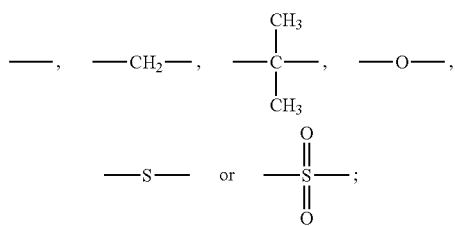

Z is

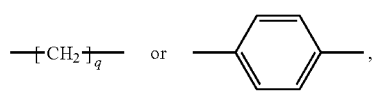

wherein q is an integer or decimal with a value ranging from 0 to 6; and
Y is A or B, and at least one of Y is B, wherein:
A is

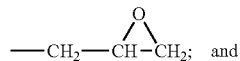

B is

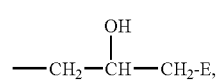

wherein
E is

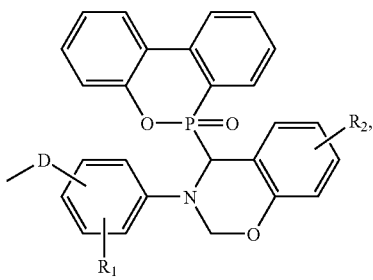

wherein:
  $R_1$ and $R_2$ are as defined in claim 1; and
  D is an ether group (—O—) or an ester group (—COO—).

5. The flame-retardant epoxy resin semi-thermoset according to claim 4, wherein the flame-retardant epoxy semi-thermoset has a structure of formula (a), and $R_3$ is methyl and $R_4$ is H.

6. The flame-retardant epoxy resin semi-thermoset according to claim 5, containing phosphorous of 0.5-4 wt %.

7. The flame-retardant epoxy resin semi-thermoset according to claim 6, containing phosphorous of 1-2 wt %.

8. The flame-retardant epoxy resin semi-thermoset according to claim 4, wherein the flame-retardant epoxy semi-thermoset has a structure of formula (b), and Q is —C(CH$_3$)$_2$—.

9. The flame-retardant epoxy resin semi-thermoset according to claim 8, containing phosphorous of 0.5-4 wt %.

10. The flame-retardant epoxy resin semi-thermoset according to claim 9, containing phosphorous of 1-2 wt %.

11. A process for preparing a phosphorous-containing flame-retardant epoxy resin semi-thermoset according to claim 4, comprising reacting the compound of formula I

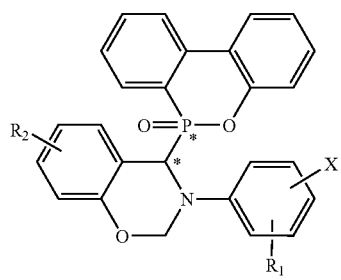
I wherein:
R$_1$ and R$_2$ are independently H, C$_1$-C$_4$ alkyl, CF$_3$, OCF$_3$, phenyl, halogen, phenoxy, C$_3$-C$_7$ cycloalkyl, or C$_1$-C$_4$ alkoxy; and
X is carboxyl or hydroxyl,
with an epoxy resin having a structure selected from the group consisting of formulae (a') to (f'):

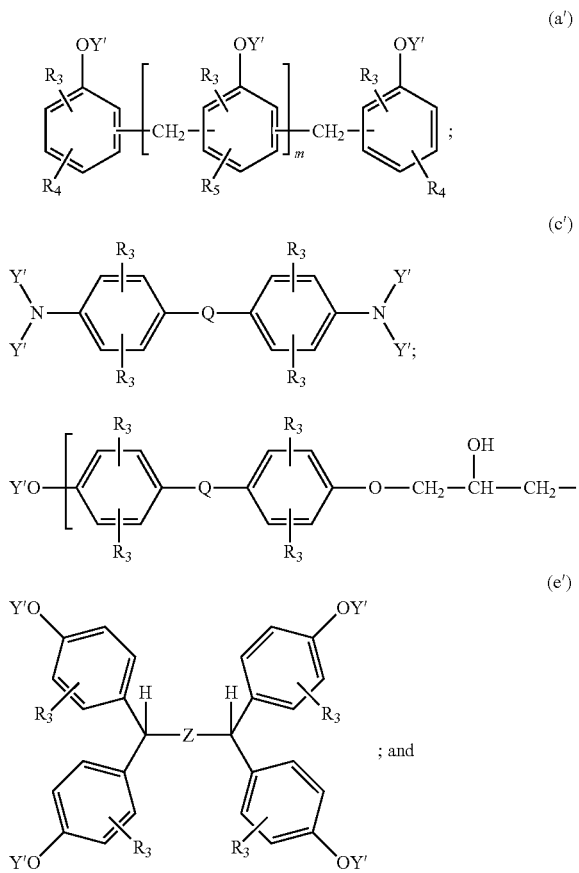

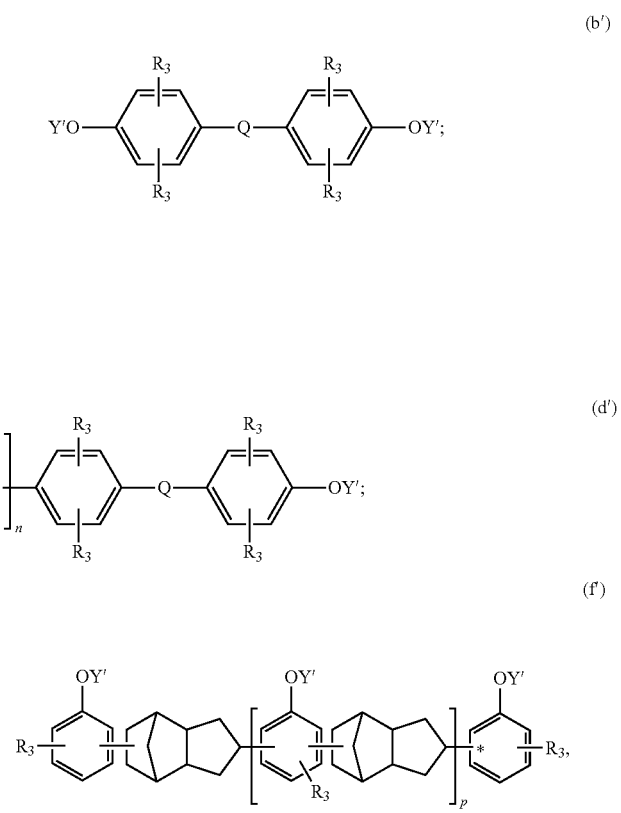

wherein m, n, p, R$_3$, R$_4$, R$_5$, Q and Z are as defined in claim 4; and
Y' is

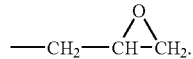

12. The process according to claim 11, wherein the reaction is carried out at a temperature of 100° C. to 200° C.

13. The process according to claim 11, wherein the reaction is carried out in the presence of a catalyst selected from the group consisting of phenylimidazole, dimethylimidazole, triphenylphosphine, quarternary phosphonium compounds, and quarternary ammonium compounds.

14. A phosphorus-containing flame-retardant epoxy resin thermoset, manufactured by curing the phosphorus-containing flame-retardant epoxy resin semi-thermoset according to claim 4.

15. The flame-retardant epoxy resin thermoset according to claim 14, wherein the flame-retardant epoxy resin semi-thermoset is automatically cured.

16. The flame-retardant epoxy resin thermoset according to claim 14, wherein the flame-retardant epoxy resin semi-thermoset is cured by a curing agent.

17. The flame-retardant epoxy resin thermoset according to claim 16, wherein the curing agent is selected from the group consisting of phenol novolac, dicyandiamide, diaminodiphenyl methane, diaminodiphenyl sulfone, phthalic anhydride, and hexahydrophthalic anhydride.

18. The flame-retardant epoxy resin thermoset according to claim 14, wherein the flame-retardant epoxy resin semi-thermoset is cured at a temperature higher than 150° C. with equal equivalent of the curing agent.

19. The flame-retardant epoxy resin thermoset according to claim 14, wherein the flame-retardant epoxy resin semi-thermoset has a structure of formula (a), and R$_3$ is methyl and R$_4$ is H.

20. The flame-retardant epoxy resin thermoset according to claim 19, containing phosphorous of 0.5-4 wt %.

21. The flame-retardant epoxy resin thermoset according to claim 20, containing phosphorous of 1-2 wt %.

22. The flame-retardant epoxy resin thermoset according to claim 14, wherein the flame-retardant epoxy resin semi-thermoset has a structure of formula (b), and Q is —C(CH$_3$)$_2$—.

23. The flame-retardant epoxy resin thermoset according to claim 22, containing phosphorous of 0.5-4 wt %.

24. The flame-retardant epoxy resin thermoset according to claim 23, containing phosphorous of 1-2 wt %.

* * * * *